United States Patent [19]

Martin et al.

[11] 4,240,987
[45] Dec. 23, 1980

[54] CHEMICAL PROCESS

[75] Inventors: Trevor I. Martin, Burlington; Paul Szabo, Islington, both of Canada; Sam R. Turner, Webster, N.Y.

[73] Assignee: Xerox Corporation, Stamford, Conn.

[21] Appl. No.: 88,895

[22] Filed: Oct. 29, 1979

[51] Int. Cl.³ .......................................... C07C 25/26
[52] U.S. Cl. .................................................. 570/206
[58] Field of Search ................................. 260/649 DP

[56] References Cited

U.S. PATENT DOCUMENTS 4,007,221  2/1977  Urbach .......................... 260/649 DP

OTHER PUBLICATIONS

Baird et al. ACS Div. of Petrol. Chem., 15,3, B 73–81 (1970).
Novikov, Obshcher Kim, 29, 58–59 (1959) [C.A., 53, 21797g].
Pearson et al., Synthesis, Sep. 1976, pp. 621–623.
Chem. Abs. 76, 126650z (1972).
Wirth et al., Ann., 634, pp. 84–104 (1960).
Kern et al. Mekromolekulare Chemie, 29, 164, (1959).

Primary Examiner—Curtis R. Davis

[57] ABSTRACT

There is disclosed a process for the direct iodination of polyarylidene compounds to provide highly pure para-substituted diiodo derivatives. The polyarylidene compound is reacted with iodine in the presence of an oxidant, unreactive with the aromatic nucleus, in a reaction medium containing a solvent for the polyarylidene compound, a catalyst and water. The reaction medium is recovered for reuse in subsequent reactions by the removal of spent oxidant which, in the preferred embodiment, is based upon the temperature dependent differences in solubility between the diiodo derivative and the spent oxidant.

17 Claims, 5 Drawing Figures

CHEMICAL PROCESS

This invention relates to a process for the direct iodination of polyarylidene compounds and more particularly to the production of highly pure 4,4'-diiodobiphenyl.

The production of diiodobiphenyl in the past has involved both the direct and indirect iodination of biphenyl. The indirect method involves a biphenyl derivative which has been previously provided with reactive sites on the biphenyl nucleus. One such well known method involves the diazotization of benzidine followed by reaction with potassium iodide to provide diiodobiphenyl. Since benzidine has been recognized as a potent carcinogen, this reaction is no longer feasible on a large scale.

Most prior art methods for the direct iodination of biphenyl have provided poor yields and highly impure crude products which were difficult to purify. For example, a process which provides diiodobiphenyl by direct iodination is described by A. N. Novikov in the publication Zhur. Obshcher Kim., 29, 58–9 (1959) reported in "Chemical Abstracts", Vol. 53, 21797G (1959). In this process, iodine, nitric acid and sulfuric acid in a medium of acetic acid and carbon tetrachloride are reacted with biphenyl at a temperature in the range of 90°–95° C. When this reaction was attempted, a reaction product was obtained which was colored by impurities, probably the nitration product of biphenyl. This product is difficult to purify and is therefore unsuitable for large scale use.

Another process for the direct iodination of biphenyl is reported in Amer. Chem. Assoc. Div. Petrol. Chem. Prepr., 15, 3, B73-81 (1970) by W. C. Baid and J. H. Surridge. In this process, biphenyl is reacted with iodine in the presence of cupric chloride to provide monoiodobiphenyl as the major product and a smaller amount of diiodobiphenyl. When adopted for polyarylidene materials, a reaction diluent such as chlorobenzene must be used and the rate of reaction is very slow, for example, 48 hours for monoiodination of biphenyl.

Another attempt to directly react iodine and biphenyl is reported by H. O. Wirth, O. Konigstein and W. Kern in Ann. 634, 84 (1960). In this reaction, iodine and iodic acid are utilized to provide a fair yield of monoiodobiphenyl. A small amount of diiodobiphenyl was produced as a by-product. In addition, W. Kern, M. Seibel and H. O. Wirth reported the use of sodium persulfate as an oxidant for iodination of methyl substituted polyarylidenes to provide the corresponding monoiodo aromatic compound in Makromolekulare Chemie 29, 164 (1959). In both of the above references, there was no suggestion to provide diiodobiphenyl.

Another process for the direct iodination of polynuclear aromatic compounds is reported by D. E. Pearson et al. in Synthesis 621 (1976). In this process, iodine monochloride is reacted with the polynuclear aromatic compound in the presence of trimethyl phosphate. For example, fluorene was iodinated to 2,7-diiodofluorene in low yield with considerable impurity. An extremely long reaction period of about 16 hours is required, and trimethyl phosphate has undesirable toxicological properties.

Suzuki reports obtaining a relatively high yield of 4,4'-dioodobiphenyl by direct iodination of biphenyl with iodine utilizing periodic acid as an oxidant in "Chemical Abstracts", Vol. 76, 126650Z (1972). The oxidant is extremely expensive and large amounts of waste products must be disposed of should such a process be utilized in large scale.

Accordingly, there is needed a convenient process for the production of highly pure para-substituted polyarylidene diiodides in large amounts for commercial use. The above-mentioned diiodobiphenyl is a convenient molecule for chemical synthesis of many products useful in the electronics and the pharmaceutical arts.

BRIEF DESCRIPTION OF THE INVENTION

In accordance with this invention, there is provided a process for producing diiodinated polyarylidene compounds in high yield and purity which comprises:

(a) reacting a polyarylidene compound with iodine in the presence of an oxidant, said oxidant being unreactive with the polyarylidene compound and, in the spent form, having a profound solubility difference from the diiodinated polyarylidene compounds in a reaction medium comprising a solvent for said compound, water and a catalyst;

(b) removing spend oxidant from said reaction medium based upon the difference in solubility of the spent oxidant and the diiodinated polyarylidene compound; and (c) recycling the reaction medium from step (b) to a reactor and repeating step (a).

As indicated above, there are many known methods for producing diiodinated polyarylidene compounds. The most difficult aspect has been to provide a combination of high purity and yield with economically and ecologically safe results. There has now been developed such a process which involves the recycling of the reaction medium rendered suitable for further use by the convenient removal of spent oxidant. As will be more particularly pointed out below, the removal of the spent oxidant is critical to continued high yields upon reuse of the reaction medium in the subject reaction.

As is known in the prior art, the direct iodination of polyarylidene compounds, usually biphenyl, involves the use of a reaction medium which includes a solvent for the compound, iodine, a catalyst and an oxidant. The majority of the reaction medium, by volume, is the solvent, normally an organic acid such as acetic acid.

The process of this invention typically utilizes a strong mineral acid as a catalyst. Typically, sulfuric acid is employed although other mineral acids such as hydrochloric and phosphoric acid can also be used. The reaction of iodine and biphenyl in accordance with this invention can proceed without the use of a catalyst, but the rate of reaction is greatly decreased, such as by a factor of about 10. Typically, the amount of mineral acid employed is in the range of from about 25 percent to about 100 percent by weight based upon the weight of the polyarylidene compound.

While different polyarylidene compounds are utilized in the process of this invention, the compound of greatest interest is biphenyl. A biphenyl having its 4 and 4' positions occupied by iodine is highly desirable as an intermediate when available at low cost and high purity. Other polyarylidene compounds include terphenyl, quaterphenyl, quinquiphenyl and sexiphenyl.

Another class of compounds employed in the process of this invention are condensed polycyclic compounds such as anthracene, naphthalene, pyrene and fluorene. The condensed polycyclic compounds also react with iodine to form diiodo derivatives in accordance with the process of this invention. Accordingly, one may replace the above-mentioned polyarylidene compounds in the process of this invention and achieve the advantageous results as specified herein.

Although not recognized as a catalyst, the reaction time is greatly increased by the addition of a small amount of water. An increase by a factor of 40 in reaction rate has been observed in the process of this invention over the same reaction conducted in the complete absence of water. While not intending to limit the invention in any way, the water is believed to increase the solubility of the oxidant in the reaction medium thereby increasing the reaction rate. The reaction medium typically contains in the range of from about 5 to about 40 percent by weight water and preferably in the range of from about 15 to about 25 percent.

Typically, the reactants are combined in a reactor and heated to a temperature in the range of from about 70° C. to about 90° C. As will be more fully described below in the examples, the reaction proceeds quickly and nearly to completion within about 1 to about 2 hours, typically about 1.25 hours. However, in large scale operations, one may desire to continue the reaction for an additional time period to assure complete reaction. Continuing the reaction, for example, up to about 3 hours will not harm the product and will approach completion of the reaction.

One of the most advantageous features of the process of this invention is that the reaction medium, if properly treated in accordance with the teachings of this invention, can be recycled indefinitely, thereby effecting great savings and eliminating the ecological problem of discarding large amounts of waste. By a series of operations, the reaction medium is substantially recovered and reused with no decrease in reaction rate as will be more fully described below.

In accordance with this invention, the reaction product is recovered from the reaction medium in high yield by filtration since the diiodo derivative is insoluble in the reaction medium. However, in order to reuse the reaction medium, the spent oxidant must also be removed. The removal of the spent oxidant can be accomplished by utilizing the solubility differences at various temperatures between the spent oxidant and the desired diiodo derivative.

In the preferred embodiment, the diiodo derivative is first removed from the reaction medium by filtration of the medium while at an elevated temperature near the reaction temperature so as to retain the spent oxidant in solution. The filtrate, containing spent oxidant in solution is then cooled causing the spent oxidant to precipitate. Another filtration of the reaction medium conveniently removes the spent oxidant. The filtrate is thus ready for reuse by adding fresh oxidant, iodine, polyarylidene compound and make-up reaction medium.

In another embodiment, the reaction medium is cooled immediately following the termination of the iodination reaction. There is thus produced a precipitate which is a mixture of spent oxidant and diiodo derivative. The precipitate mixture is removed from the reaction medium by filtration providing a filtrate reusable in further iodination reaction as mentioned above. Since the spent oxidant is readily soluble in water, it is separated from the essentially water insoluble diiodo derivative by slurrying the mixed precipitate in water. The desired diiodo derivative is conveniently recovered by filtration.

The diiodo derivative is purified by one or more alcohol washes, such as for example, methanol. With such alcohol washing, the diiodo derivative is recovered having a purity in excess of 99 percent by weight.

BRIEF DESCRIPTION OF THE DRAWINGS

The process of this invention will be further described with respect to the attached drawings wherein.

DETAILED DESCRIPTION OF THE DRAWINGS

Figure 1:
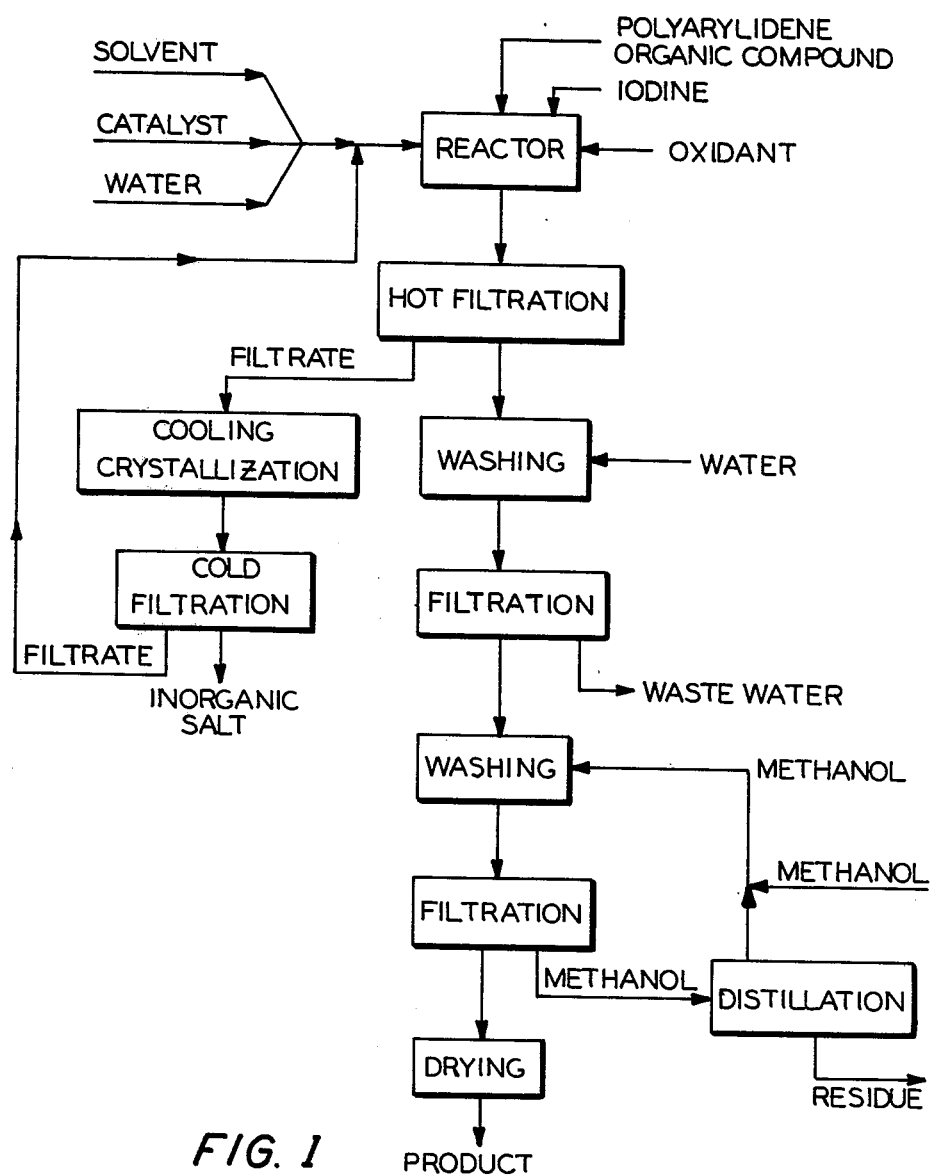
FIG. 1 is a flow chart illustrating the purification steps and recycling means for the reaction medium.

In FIG. 1, there are shown by block diagram, the various steps of a typical process of this invention indicating an advantageous recirculation of the reaction medium. Referring now to FIG. 1, a suitable reactor is charged with a polyarylidene compound, for example, biphenyl, iodine, an oxidant, and a reaction medium comprising water, catalyst and an organic acid. After a suitable reaction time in the range of from about 60 to 90 minutes at a temperature in the range of from about 70°–90° C., the reaction product is filtered while at or near the reaction temperature. When the preferred oxidant, a persulfate, is employed, the spent oxidant in the hot filtrate is a dissolved sulfate. As is indicated in FIG. 1, the filtrate is cooled to produce crystallization of the inorganic salt whereupon the salt is separated by filtration and the filtrate recycled to the reactor for reuse.

The filter cake from the hot filtration, containing the desired product, is then washed with water, filtered again and washed with methanol which dissolves any polyiodo by-products present. Subsequent to the methanol wash, the product is again filtered and the methanol recovered for recycling. The filter cake is dried yielding the highly pure para-substituted polyarylidene compound.

Figure 2:
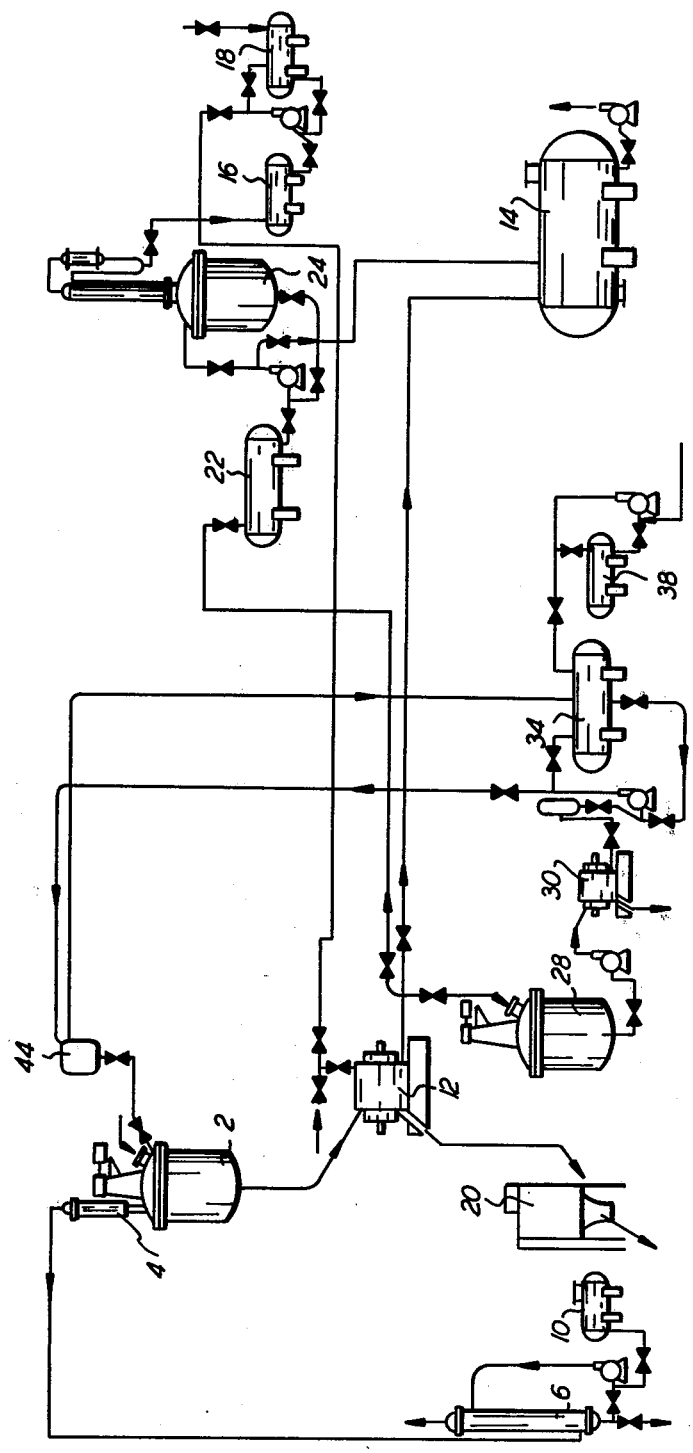
FIG. 2 is a schematic diagram of a typical process flow sheet illustrating the equipment utilized in the process of this invention.

In FIG. 2, there is shown a process flow sheet indicating the preferred manner in which the process of this invention is carried out to provide, for example, 4,4'-diiodobiphenyl. In practice, the equipment is glass lined steel or acid resistant stainless steel.

In FIG. 2, reactor 2 is equipped with a mechanical stirrer and a reflux condenser 4. Traces of iodine vapor are passed to a packed column 6 supplied with sodium hydroxide solution from tank 10. Stirring the reaction mixture has been found to be necessary in that the agitation encourages initiation of precipitation of the iodinated product.

After completion of the reaction, the reaction mixture is then transferred in the form of a fine slurry into filter 12. Filter 12 is equipped so as to maintain the temperature of the slurry at about the reaction temperature during the filtration procedure. The filter cake is washed with water which is then discarded periodically through tank 14. The filter cake is then washed with methanol supplied from tanks 16 and 18, then transferred to dryer 20. The dried product from dryer 20 is usually 99.5 percent pure making the product highly desirable for use as an intermediate to produce fine chemicals.

The methanol washings contain about 2 percent by weight of organic byproducts and a small amount of water. The methanol washings are transferred to tank 22 for periodic recovery through subsequent transfer to distillation vessel 24. The residue from the distillation vessel 24 is transferred to tank 14 for disposal while recovered methanol is transferred to tank 16.

The hot filtrate from filter 12 is transferred to crystallizer 28 wherein it is cooled to approximately room temperature with stirring. The cooled filtrate is maintained at room temperature for a period of about 2 hours. The spent oxidant in the form of an inorganic salt is caused to precipitate in the cooled filtrate, and the slurry is transferred to centrifuge filter 30. The filter cake is discharged to waste, and the cold filtrate from centrifuge filter 30 is transferred to tank 34.

The cold filtrate in tank 34 is restored as a reaction medium by transferring the appropriate amount of solvent, catalyst and water from makeup tank 38. Tank 38 is supplied with the necessary materials from a source not shown in FIG. 2. The full strength reaction mixture in tank 34 is then transferred to reactor 2 through a measuring tank 44. The reaction mixture is charged with the appropriate amount of iodine, biphenyl and oxidant, then brought up to reaction temperature. The process is then repeated for subsequent production for 4,4'-diiodobiphenyl.

DESCRIPTION OF THE PREFERRED EMBODIMENTS

To further define the specifics of the present invention, the following examples are intended to illustrate and not limit the subject matter of the present invention. Parts and percentages are by weight unless otherwise indicated.

EXAMPLE I

Into a suitable reactor is placed about 1.35 moles of biphenyl, 1.48 moles of iodine and about 1.89 moles of ammonium persulfate. A reaction medium comprising either a recycled, previously used reaction medium or a fresh mixture is prepared to equal a volume of about 2.25 liters comprising 360 ml. of water, 1,800 ml. of glacial acetic acid, and 81 ml. of concentrated sulfuric acid. The reaction mixture is heated to about 80° C. Because of the exothermicity of the reaction, the temperature of the reaction medium rises to about 85° C. for about 10 minutes and returns to the controlled temperature of about 80° C. The reaction mixture is stirred vigorously for about 90 minutes at about 80° C.

Figure 3:
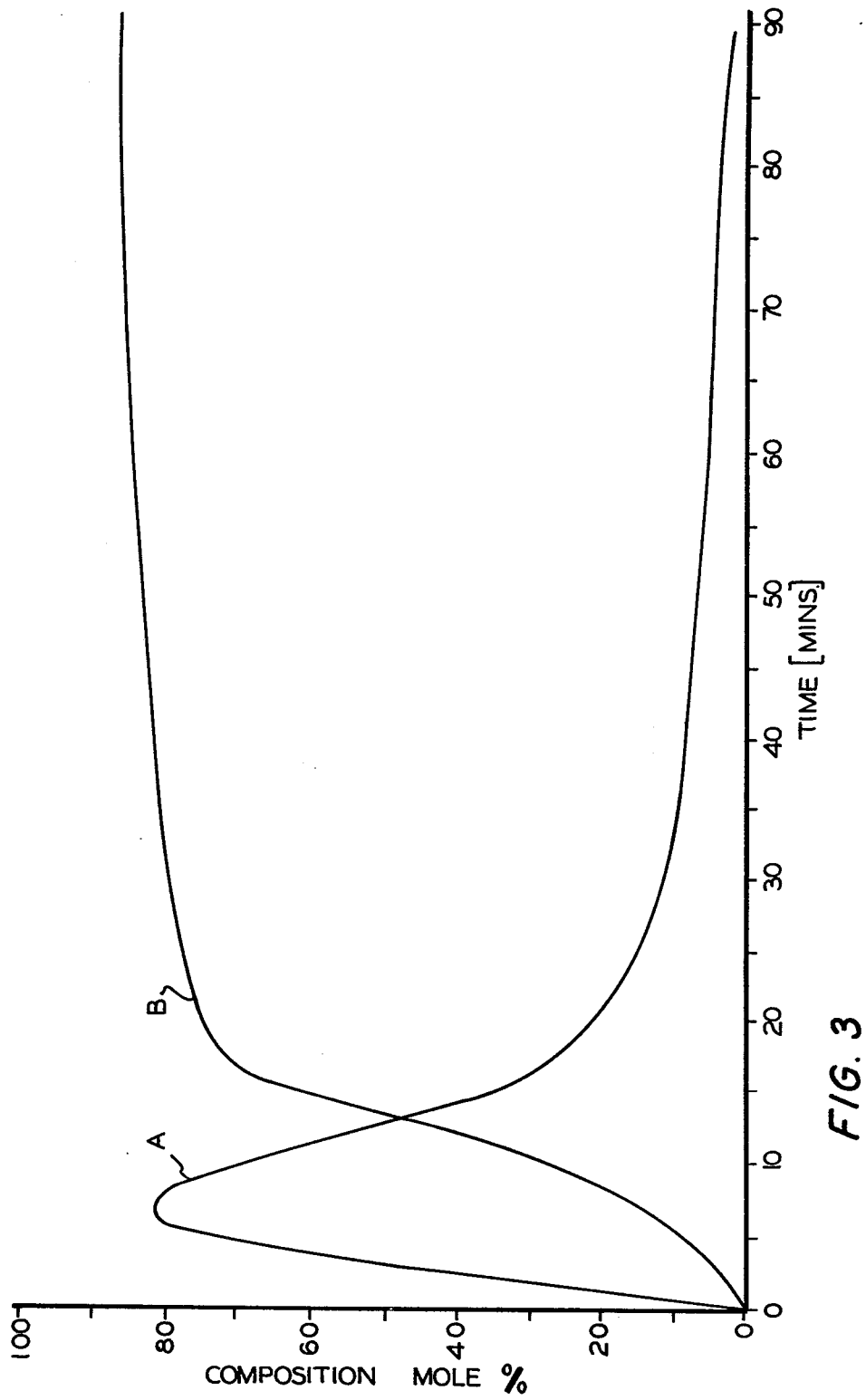
FIG. 3 is a graphic representation of a typical reaction in accordance with the process of this invention indicating the composition of the reaction mixture in mole percent with respect to time.

During the reaction, samples of reaction mixture are extracted for analysis to determine the composition of the reaction mixture in mole percent of 4-iodobiphenyl and 4,4'-diiodobiphenyl. The results of the analysis are presented in FIG. 3 as curves A and B, respectively. As is indicated in FIG. 3, the reaction is substantially complete after about 40 minutes.

The reaction mixture is filtered while maintained at or near the temperature of reaction in order to remove the diiodobiphenyl. The product cake is subsequently washed with water to remove residual acidic impurities, then twice with methanol (2,000 ml each wash), and dried to yield 500 g (1.2 mole) of 4,4'-diiodobiphenyl (99.5 percent pure).

The filtrate is cooled to room temperature thereby causing the spent oxidant, ammonium sulfate, to precipitate. The spent oxidant is removed from the reaction medium by filtration at room temperature. The reaction medium is brought up to the desired quantity for reuse in a subsequent reaction.

Figure 4:
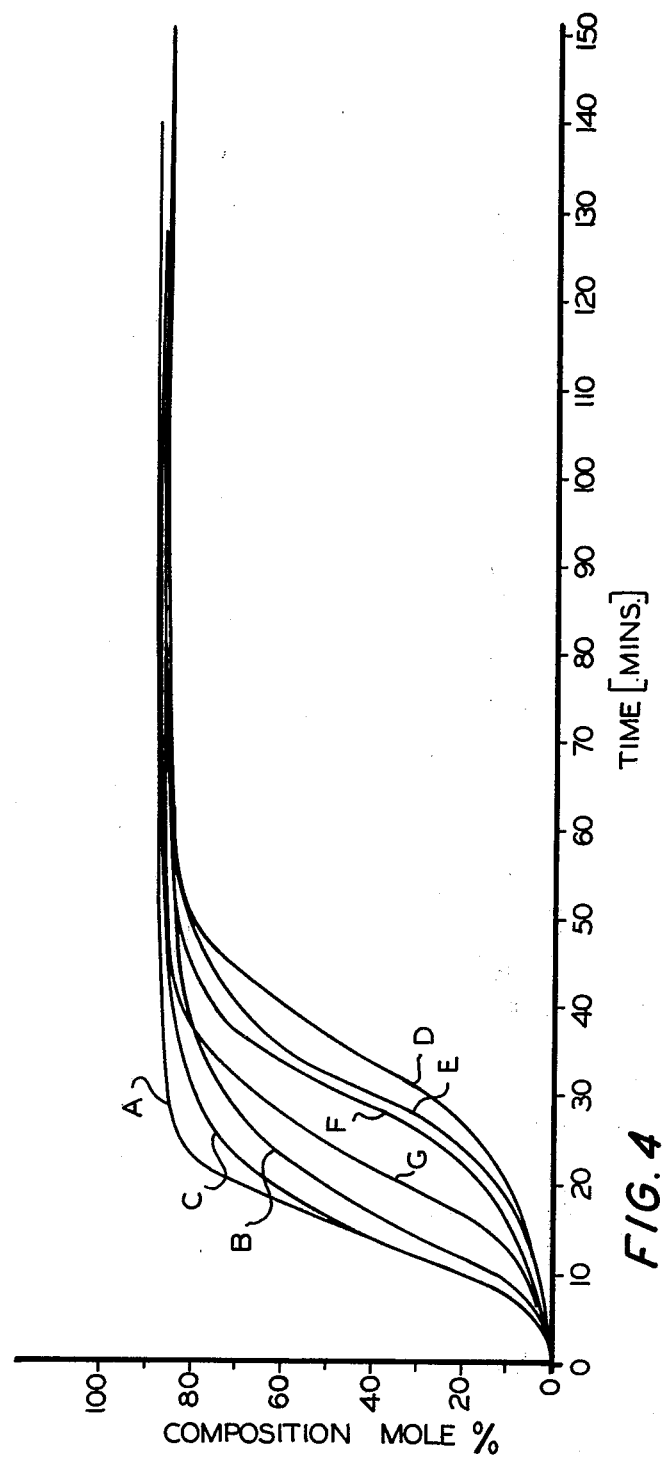
FIG. 4 is a graphic representation of a series of reactions wherein the reaction medium is reused in accordance with this invention.
Figure 5:
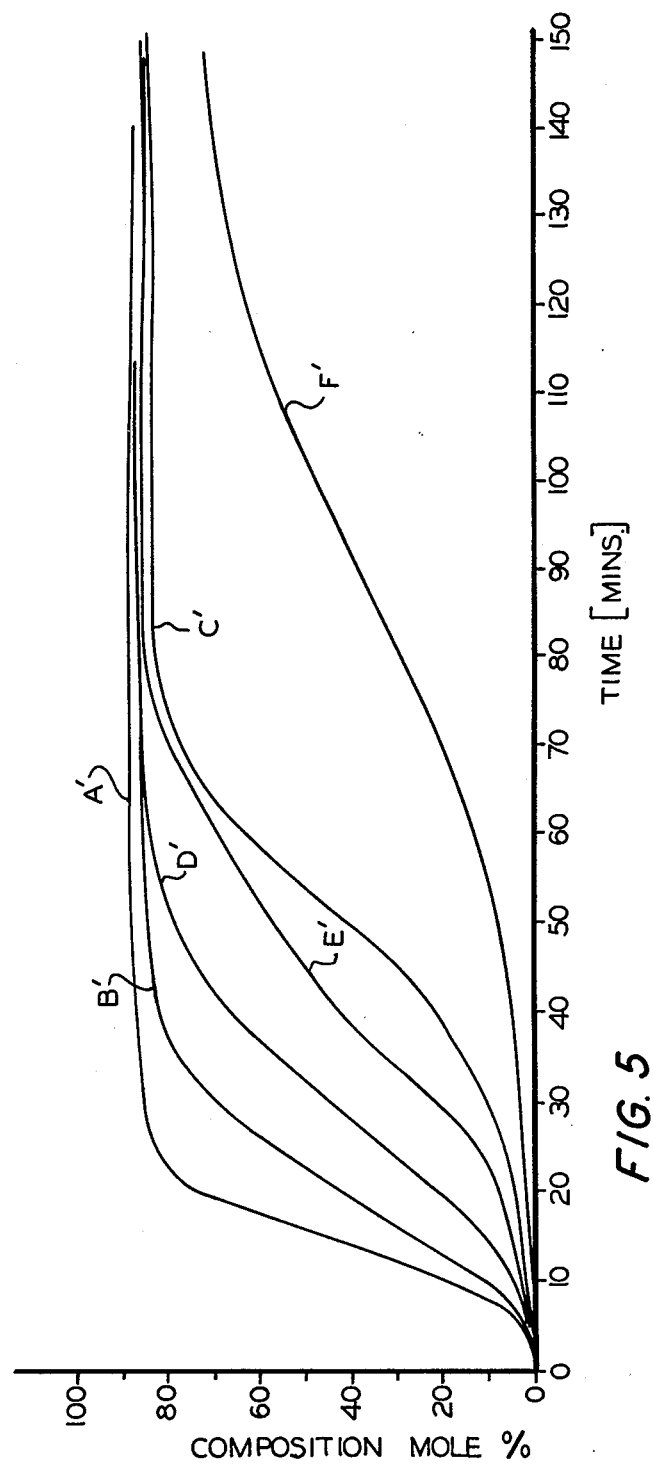
FIG. 5 is a graphic representation of a reaction series wherein the reaction medium is reused without removal of spent oxidant.

A series of 10 recirculations using the above procedure were performed. Illustrated in FIG. 4 are curves A–F and G indicating the amount of 4,4'-diiodobiphenyl in the reaction mixture as mole percent. Curves A–F represent the reaction profile for the first through the fifth reaction while curve G represents the profile of the tenth reaction wherein the reaction medium is recirculated. A comparison between this series of recirculations can be made with a similar series of recirculations where the spent oxidant was not removed prior to each reaction as shown in FIG. 5, curves A'–F' indicating the amount of 4,4'-diiodobiphenyl in the reaction mixture as mole percent. Clearly, the reaction profile remains constant over the series of ten recirculations where the spent oxidant was being removed prior to each reaction (FIG. 4) as opposed to the drastic decrease in reaction rate observed when the spent oxidant was not removed but allowed to accumulate (FIG. 5).

EXAMPLE II

Into a suitable reactor there are charged 0.1 mole of p-terphenyl, 0.109 mole of iodine and 0.14 mole of ammonium persulfate. Also added to the reactor is a reaction medium comprising 165 ml. glacial acetic acid, 7.4 ml. of sulfuric acid and 33 ml. of water. The contents of the reactor is heated to about 80° C. for about 100 minutes with stirring. While still at the elevated temperature, the reaction mixture is filtered to recover 4,4''-diiodoterphenyl which is purified by washing with methanol. The filtrate is cooled to precipitate the spent oxidant, as in Example I, to recover the reaction medium for reuse in the above-described reaction.

EXAMPLE III

Example II is repeated with the exception that p-terphenyl is replaced by pyrene to provide upon filtration of the reaction mixture 1,6-diiodopyrene. The reaction medium is recovered as in Example I.

EXAMPLE IV

The process of Example II is repeated with the exception that p-terphenyl is replaced with fluorene. Upon filtration of the reaction mixture, while still at the reaction temperature, there was recovered 2,7-diiodofluorene having a melting point of 212° C. The reaction medium is recovered as described in Example I for reuse in the reaction.

What is claimed is:
1. A process for producing diiodinated polyarylidene compounds in high yield and purity which comprises:
 (a) reacting in a suitable reactor, a polyarylidene compound with iodine in the presence of an oxidant, said oxidant being unreactive with said compound in a reaction medium comprising a solvent for said compound, water and a catalyst;
 (b) recovering the reaction medium for reuse in step (a) by the steps of:
  (i) removing the diiodinated aromatic compound;
  (ii) precipitating the spent oxidant; and

(iii) removing the precipitated spent oxidant from the reaction medium; and (c) recycling the reaction medium to the reactor and repeating step (a).

2. The process of claim 1 wherein the polyarylidene compound is biphenyl.

3. The process of claim 1 further including the step of purifying the diiodinated aromatic compound by washing with alcohol.

4. The process of claim 2 further including the step of purifying the diiodobiphenyl by washing with alcohol.

5. The process of claim 4 wherein the alcohol is methanol.

6. The process of claim 1 wherein the oxidant is a persulfate.

7. The process of claim 6 wherein the persulfate is ammonium persulfate.

8. The process of claim 1 wherein the reaction medium is recovered by removing the diiodinated aromatic compound by filtration while said medium is held at an elevated temperature and thereafter cooling the reaction medium whereby the spent oxidant is precipitated followed by removal of the spent oxidant by filtration.

9. The process of claim 1 wherein the reaction medium is recovered by cooling the contents of the reactor thereby precipitating the spent oxidant, separating the spent oxidant together with diiodinated compound from the reaction medium by filtration.

10. The process of claim 9 further including the step of separating the spent oxidant from the diiodinated aromatic compound by dissolving the spent oxidant selectively and filtering the mixture.

11. The process of claim 10 further including the step of purifying the diiodinated aromatic compound subsequent to separation from the spent oxidant by washing with alcohol.

12. The process of claim 11 wherein the alcohol is methanol.

13. The process for preparing 4,4'-diiodobiphenyl which comprises:

(a) reacting unsubstituted biphenyl with iodine in the presence of an oxidant unreactive with said biphenyl in a reaction medium comprising a solvent for said biphenyl, a mineral acid catalyst and water;

(b) filtering the resultant mixture subsequent to the reaction to remove 4,4'-diiodobiphenyl at a temperature which retains the spent oxidant in solution;

(c) cooling the filtrate thereby precipitating the spent oxidant; and (d) removing the spent oxidant from the reaction medium.

14. The process of claim 13 further including the steps of recycling the reaction medium subsequent to the removal of spent oxidant to a reactor and recharging the reaction medium with biphenyl, iodine, oxidant and additional reaction medium containing a catalyst, water and solvent so as to repeat the reaction.

15. The process of claim 14 wherein the oxidant is a persulfate.

16. The process of claim 15 wherein the persulfate is ammonium persulfate.

17. A process for producing diiodinated polycyclic compounds in high yield and purity which comprises:

(a) reacting in a suitable reactor, a polycyclic compound with iodine in the presence of an oxidant, said oxidant being unreactive with said compound in a reaction medium comprising a solvent for said compound, water and a catalyst;

(b) recovering the reaction medium for reuse in step (a) by the steps of:
(i) removing the diiodinated aromatic compound;
(ii) precipitating the spent oxidant; and
(iii) removing the precipitated spent oxidant from the reaction medium; and (c) recycling the reaction medium to the reaction and repeating step (a).

* * * * *